(12) United States Patent
Corcoran et al.

(10) Patent No.: US 7,527,147 B2
(45) Date of Patent: May 5, 2009

(54) PACKAGING AND ORGANIZING ORTHODONTIC APPLIANCES FOR LOADING OF SET-UP TRAYS THEREWITH

(75) Inventors: Kevin Corcoran, Corona, CA (US); John Payne, Huntington Beach, CA (US)

(73) Assignee: Ormco Corporation, Orange, CA (US)

( * ) Notice: Subject to any disclaimer, the term of this patent is extended or adjusted under 35 U.S.C. 154(b) by 275 days.

(21) Appl. No.: 10/781,138

(22) Filed: Feb. 18, 2004

(65) Prior Publication Data

US 2005/0178685 A1 Aug. 18, 2005

(51) Int. Cl.
*B65D 83/10* (2006.01)
(52) U.S. Cl. .................. 206/63.5; 206/369
(58) Field of Classification Search .............. 206/63.5, 206/83, 557, 570, 562–565, 368, 369, 499, 206/536, 732–734; 433/2, 8, 9, 25, 49, 77, 433/79
See application file for complete search history.

(56) References Cited

U.S. PATENT DOCUMENTS

| 622,396 | A | * | 4/1899 | Roberts .................. 206/734 |
| 4,085,845 | A | * | 4/1978 | Perfect .................. 206/564 |
| 4,153,160 | A | * | 5/1979 | Leigh .................... 206/564 |
| 4,191,291 | A | * | 3/1980 | Brown ................... 206/369 |
| 4,898,276 | A | * | 2/1990 | Georgakis ............... 206/369 |
| 5,199,567 | A | | 4/1993 | Discko, Jr. |
| 5,221,202 | A | | 6/1993 | James |
| 5,328,363 | A | | 7/1994 | Chester et al. |
| 5,348,154 | A | | 9/1994 | Jacobs et al. |
| 5,350,059 | A | | 9/1994 | Chester et al. |
| 5,542,844 | A | | 8/1996 | Perret, Jr. |
| 5,636,736 | A | | 6/1997 | Jacobs et al. |
| 5,692,896 | A | | 12/1997 | Pospisil et al. |
| 5,697,780 | A | | 12/1997 | Tuneberg et al. |
| 5,756,174 | A | | 5/1998 | Tuneberg |
| 5,759,028 | A | | 6/1998 | Bozman |
| 5,762,192 | A | | 6/1998 | Jacobs et al. |
| 5,823,773 | A | | 10/1998 | Brysch |
| 5,827,058 | A | * | 10/1998 | Kelly et al. ............... 433/9 |
| 6,213,767 | B1 | | 4/2001 | Dixon et al. |
| 6,415,916 | B1 | * | 7/2002 | Rini ........................ 206/83 |
| 6,482,003 | B2 | | 11/2002 | Dixon et al. |
| 2005/0205460 | A1 | * | 9/2005 | Atkin et al. ............ 206/368 |
| 2006/0054515 | A1 | * | 3/2006 | Corcoran ............... 206/63.5 |

* cited by examiner

Primary Examiner—J. Gregory Pickett
(74) Attorney, Agent, or Firm—Wood, Herron & Evans, L.L.P.

(57) ABSTRACT

A system and method are provided for organizing and loading orthodontic appliances, for example orthodontic brackets, onto set-up trays. The system includes an organizer tray which holds a set-up tray in a fixed orientation, and also holds a plurality of packages of orthodontic brackets in predetermined relationships to bracket staging areas on the set-up tray. Bracket packages and the organizer tray are configured so that the brackets are presented in the same orientation, when in their packages held by the organizer tray, as they will have when transferred to the set-up tray. As a result, the brackets can be loaded onto the set-up tray from the packages without re-orientation. The organizer tray has a storage base that holds supplies of packages of the different brackets of a given set so that the organizer tray can be reloaded with packages. Preferred organizer tray and package configurations are also provided.

16 Claims, 8 Drawing Sheets

PACKAGING AND ORGANIZING ORTHODONTIC APPLIANCES FOR LOADING OF SET-UP TRAYS THEREWITH

This invention relates to the packaging of dental appliances, particularly orthodontic appliances, and to the organizing of the appliances for their loading onto set-up trays. The invention particularly relates to methods of packaging and organizing of the appliances and of loading set-up trays with the appliances, and to the packages, organizers and set-up trays and appliance packaging, loading and organizing systems.

BACKGROUND OF THE INVENTION

In the practice of dentistry, the efficient use of a dentist's time is enhanced by preparing the equipment and supplies needed by the dentist for a scheduled patient visit in advance of appointment, so that the dentist may proceed directly with an examination or treatment. The preparation is typically done by a technician or assistant on the dentist's staff. As a result, the dentist may see more patients in a specified period of time than would be possible if the dentist were to personally assemble the items.

Orthodontic practitioners, for example, have a number of examination or treatment activities, each of which may require different tools or supplies. A common task for an orthodontist is the installation of an orthodontic appliance on a patient. Currently, a most effective and widely used orthodontic appliance is an orthodontic brace that is formed of an archwire and a number of orthodontic brackets. Installation of such an appliance involves the bonding of the individual brackets of a set, each specific one to a given one of the patient's teeth. For such an installation, a set of brackets must be assembled for the orthodontist, along with adhesives, primers and other chemical substances, plus tweezers, curing light guns and other tools needed for the appliance installation.

The installation of a bracket-archwire appliance requires careful selection and placement of individual brackets from a supply thereof onto the crown of a patient's teeth in a one-by-one transfer of the brackets from the supply to the patient. The transfer involves the engagement of the correct bracket for a given tooth and the proper orientation of the bracket for placement on the appropriate tooth. Since the brackets are each tooth-specific, with each having a geometry specially configured to fit the surface of a tooth and to engage an archwire to exert specific forces on the tooth, an error in the selection of a bracket can be costly in terms of treatment time and loss of treatment quality.

Placement of a bracket on a patient's tooth requires the holding of the bracket by the orthodontist, usually with a pair of tweezers designed for that purpose, with the base of the bracket coated with adhesive and oriented for placement against the patient's tooth. Each bracket base may be considered as having four sides, one intended as the gingival side that must face the gum when mounted on the tooth with the opposite intended as the occlusal side which will face the occlusal plane. At right angles to these are the opposite sides intended as the mesial and distal sides, which must face the mesial and distal sides of the tooth, respectively. This requires proper orientation of the bracket in the hand of the orthodontist, with the gingival side facing downward for lower teeth and facing upward for the upper teeth.

Historically, an orthodontist stocks a plurality of brackets for each tooth, which have been often supplied loose in boxes. Each bracket was retrieved from a respective one of the boxes and oriented for application to the patient's tooth. When the orthodontist undertakes to retrieve the brackets from the boxes at chair-side, considerable professional time is consumed, while care must be taken to insure that the correct bracket is retrieved for a given tooth and is oriented correctly to have its pad coated with adhesive and applied to the tooth. The orthodontist will typically stock one type or model of appliance that is most commonly suitable for a patient, plus alternative types or sizes for use as the case may indicate.

The trend toward the use of a set-up tray has resulted in better use of the orthodontist's chair-side time in installing orthodontic appliances. This time has been replaced by technician or assistant time in loading the set-up trays employing many of the same motions and careful attention previously employed by the orthodontist. Set-up trays are usually hand-size trays or cards having compartments or sticky adhesive-coated pad areas to hold the individual appliances in a predetermined arrangement for pick-up by the orthodontist at tray side. Set-up trays of the type that not only hold the brackets for the orthodontist but present tooth-specific, single-doses of adhesive for use with each respective bracket are described in U.S. Pat. Nos. 6,213,767 and 6,482,003. Simpler set-up trays that hold only the brackets are also common.

Whether done by the practitioner or the practitioner's assistant, the efficiency of dental practice and the reduction of error occurrence can be improved by better ways for supplying and handling dental supplies.

SUMMARY OF THE INVENTION

A primary objective of the present invention is to improve the efficiency and accuracy of dental practice, and particularly orthodontic practice.

According to certain principles of the present invention, dental appliances are provided by a manufacturer or supplier thereof packaged in a manner that promotes their efficient handling by the practitioner. According to other principles of the invention, the appliances are organized and set-up trays are loaded in a manner than requires less time and results in fewer errors than with the prior art.

According to the illustrated embodiments of the invention, orthodontic appliances, particularly tooth-specific orthodontic brackets, are packaged in a predetermined orientation in a package containing a plurality of identical brackets of a given type and for a given tooth. The package is configured as an elongated package that serves as a carrier of the brackets to an organizing tray.

Further according to the illustrated embodiments of the invention, an organizer tray is provided with slotted recesses to receive each of a plurality of carriers, each containing a different bracket of a set. The recesses are arranged on the organizer tray so as to correspond to a logical arrangement that make it clear to an experienced practitioner which one contains brackets for which tooth. The organizer tray also contains a support for a set-up tray, such as a tray of the type described in U.S. Pat. Nos. 6,213,767 or 6,482,003. These set-up trays each contain bracket support areas, one for each tooth, arranged in a logical order that suggests the corresponding tooth of a patient for which the bracket supported thereat is for. The carrier supporting recesses are arranged on the organizer tray in a one-for-one correspondence to the areas of a set-up tray supported on the organizer tray.

According to still other principles of the invention, the organizer tray is in the form of a drawer cover, which covers a drawer having a plurality of compartments each arranged in the same order as and lying below the recesses of the organizer tray when the tray is applied to cover the drawer. In each of the compartments is stored a plurality of the carriers containing the brackets in the corresponding recesses of the organizer-tray drawer-cover. The drawer constitutes the orthodontist's supply of brackets for appliances of a particular type. The orthodontist may have a plurality of such drawers, one for each type of bracket or appliance used by the orthodontist. These drawers may be stored in a supply cabinet.

In practice, pluralities of each of the brackets used by an orthodontist are supplied to the orthodontist's office and each of the drawers are stocked. When a case is scheduled for installation of an appliance on a patient, an orthodontic assistant withdraws the organizer tray containing the brackets of the type selected by the orthodontist, and, if any of the recesses is empty of a carrier containing at least one bracket, loads a carrier into that recess. The assistant also places an empty set-up tray on the support on the organizer tray. Then, the assistant uses a tweezers to remove one bracket from each carrier and transfers the bracket to a corresponding area of the set-up. Each bracket is placed on the respective area in an orientation that will enable the orthodontist to remove it without reorienting it for placement onto the patient's tooth. This orientation is preferably the same orientation that the bracket has on the carrier that is inserted into the recess on the organizer tray. The brackets were loaded into the carrier, which served as its packaging for shipment, by the appliance manufacturer to the practitioner.

The set-up tray, so loaded, maximizes the use of the time not only of the orthodontist, but of the orthodontist's assistant. Additionally, bracket orientation and selection errors are minimized.

These and other objectives and advantages of the present invention will be more readily apparent from the following detailed description.

DETAILED DESCRIPTION

In most dental practices, a set-up tray of some sort is prepared by a dental assistant and placed at chair-side next to a patient before the dental practitioner enters the treatment area for a dental appointment. This is particularly true in orthodontic practices for appointments to install orthodontic appliances on patients. In such orthodontic practices, an orthodontic set-up tray is typically loaded with orthodontic appliances that have been pre-selected by the practitioner for treatment of a patient for whom an appointment has been scheduled to install the appliance. One of several such prior art set-up trays that are in use by orthodontists is illustrated in FIG. 1.

Figure 1:
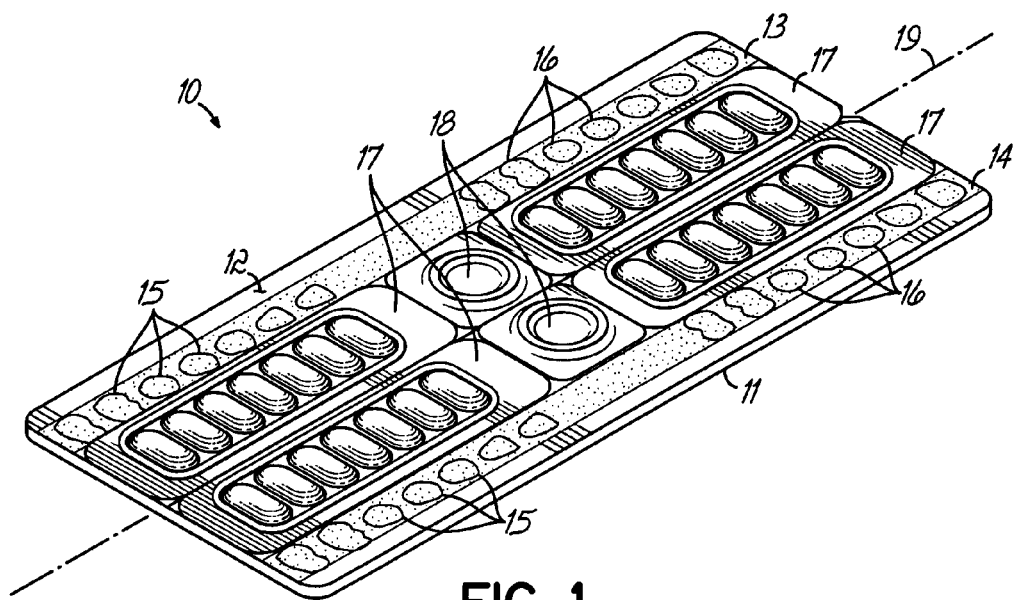
FIG. 1 is a perspective view of one version of an orthodontic set-up tray of the prior art.

In FIG. 1 is illustrated a set-up tray 10 of the type described in U.S. Pat. No. 6,482,003, hereby expressly incorporated by reference herein, and which is used in the description of the invention below. It is one prior art example of several types of set-up trays that can be used with the present invention. The particular set-up tray 10 that is illustrated and described is, in addition to being a set-up tray, a delivery system for delivering orthodontic adhesive in individual bracket doses for securing orthodontic brackets to teeth, although the adhesive delivery feature is not a necessary feature of any set-up tray for use with the present invention. The set-up tray 10 includes a resilient foam-board base 11 having a smooth plastic surface 12 that contains bracket mounting areas 13 and 14, lying on opposite sides of a centerline 19, that are coated with tacky pressure-sensitive adhesive. The area 13, when held by an orthodontist, will lie along the side of the tray 10 that faces a patient and will hold brackets 30 for the patient's upper dental arch, while the area 14 will lie along the side toward the orthodontist and will hold brackets for the patient's lower arch. The brackets 30 will be arranged on the tray in the order of the teeth in the patient's mouth, with staging areas 15 on the left side of the tray containing, from left to right, brackets for the right second molar through the right central incisor, and staging areas 16 on the right side of the tray containing, from left to right, brackets for the left central incisor through the right second molar. In the center of the tray 10 are provided enclosures 17 containing single doses of adhesive corresponding to each of the brackets, and cups 18 for holding primers or cleaning liquid.

Figure 2:
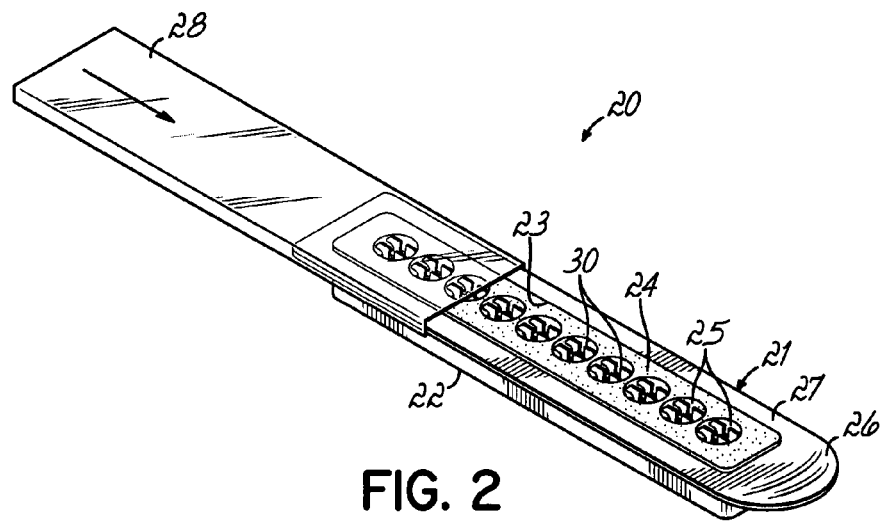
FIG. 2 is a perspective view of one embodiment of an orthodontic bracket package and carrier according to certain principles of the present invention.

FIG. 2 illustrates a package 20 embodying certain features of the present invention. The package 20 includes an elongated carrier 21 having a plastic base 22 with an elongated recess 23 formed therein. The recess 23 contains a flexible foam insert 24 having a plurality of cavities 25 therein adapted to receive and to snugly but releasably hold an orthodontic appliance, for example an orthodontic bracket 30, as illustrated in more detail in FIG. 2A. The base 22 of the carrier 21 has a tab or handle 26 formed at one end thereof that is part of a flat flange 27 that extends in a plane around the recess 23. The package 20 includes a clear plastic cover 28 that slides over the carrier 21, having internal channels formed therein into which the flange 27 of the base 22 fit. The cover 28 covers the brackets 30 and keeps them in the cavities 25 for shipment from the bracket manufacturer.

Figure 2A:
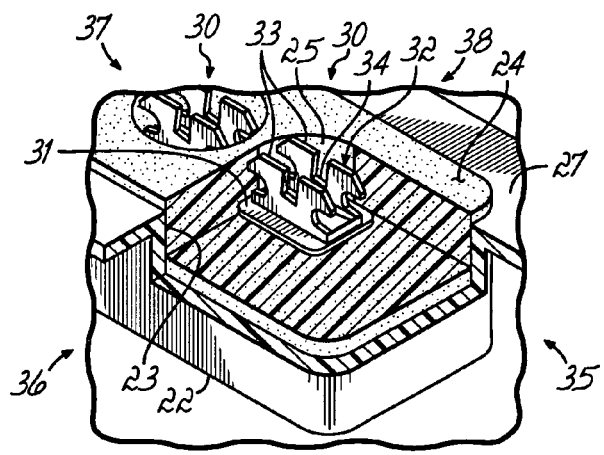
FIG. 2A is an enlarged view of a portion of the package and carrier of FIG. 2.

The brackets 30 have pads or bases 31 to which is attached or integrally formed a bracket body 32 that is typically composed of a pair of tie wings 33 in which is formed a generally horizontal archwire slot 34. As illustrated in FIGS. 2 and 2A, the brackets 30 are packaged in the cavities 25 of the carrier 21 with base 32 facing down so that the tie wings can be gripped easily with tweezers to remove the bracket from the package 20. Further, the brackets 30 may each be considered as having four sides 35-38 that include a gingival side 35 that will face the gum when the bracket 30 is mounted on a patient's tooth. The brackets 30 are inserted into the cavities of the package 20 oriented such that the gingival side 35 of the bracket 30 faces the handle or tab 26 of the carrier 21. The other sides 36-38 include, proceeding clockwise around the bracket 30, a first mesial/distal side 36, an occlusal side 37 that is opposite the gingival side 35, and a second mesial/distal side 38 that is opposite the first mesial/distal side 38.

For upper right and lower left brackets, side 36 is the mesial side of the bracket and side 38 is the distal side of the bracket; and for upper left and lower right brackets, side 36 is the distal side of the bracket and side 38 is the mesial side of the bracket.

The packages 20 have a plurality of the cavities 25 in a line. For brackets of more often used prescriptions, the number of cavities 25 in the plurality is typically seven to ten. The packages 20 may be made with other numbers of cavities 25. Three to five brackets per package may be a practical number, particularly for brackets of less often used appliance prescriptions.

Figure 3:
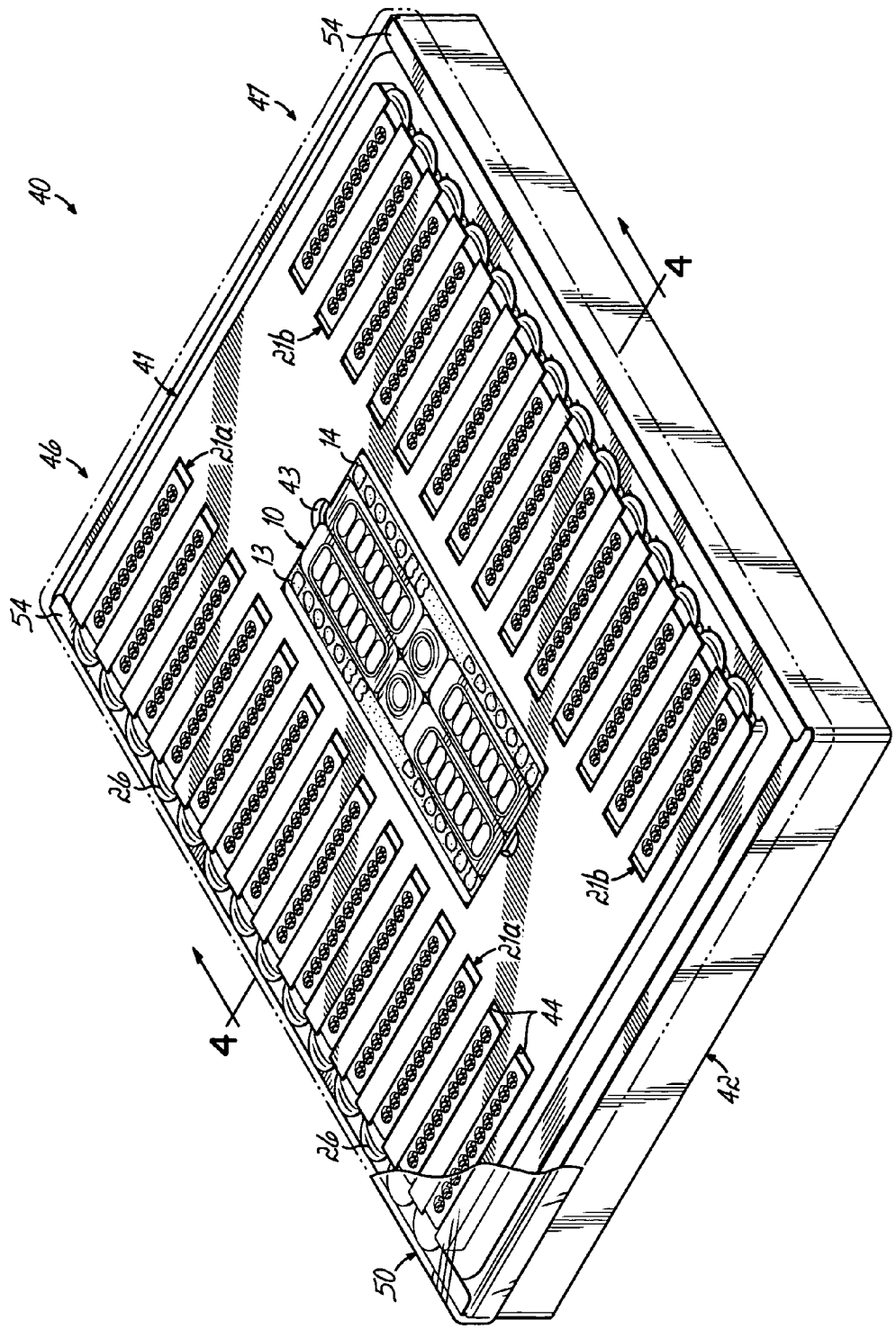
FIG. 3 is a perspective view of an orthodontic bracket organizer according to certain embodiments of the present invention, in a closed condition.

According to a method of the present invention, brackets 30 are loaded onto a set-up tray 10 from the carriers 21, illustrated as carriers and 21a and 21b, by personnel at a treating orthodontic practitioner's office with the use of an organizer 40, illustrated in FIG. 3, also according to the present invention. The organizer 40 includes an organizer tray 41 and a storage base 42. Both the organizer tray 41 and storage base 42 are each preferably made of a respective integral piece of molded plastic, although metal or other materials may be used.

The organizer tray 41 has a four-sided, set-up tray support or set-up-tray-receiving recess 43 formed at its center and a plurality of appliance holders 44. The holders are in the form of three-sided, open-ended, carrier-receiving recesses or slots, half of which are formed along one side of the organizer tray 41 and half formed along the opposite side of the organizer tray 41. The holders 44 are configured to hold the appliances, such as brackets 30, preferably in packages of appliances, such as the carriers 21. The number of the holders 44 is equal to the maximum number of brackets 30 that will form an orthodontic brace, typically twenty-eight.

Figure 3A:
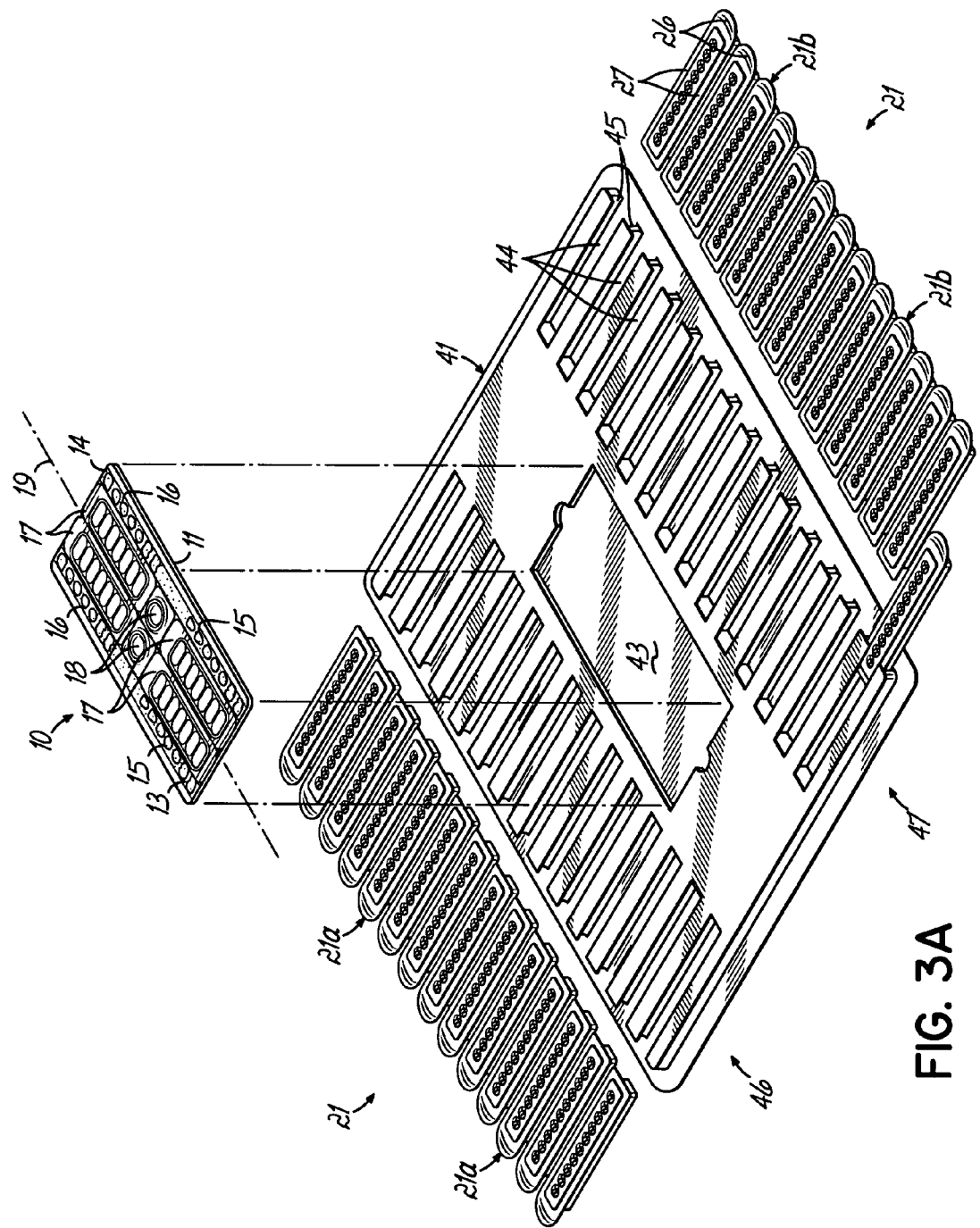
FIG. 3A is a disassembled perspective view of the upper sliding portion of the organizer of FIG. 3.

As illustrated in FIGS. 3 and 3A, the organizer tray 41 is prepared by placing in the recess 43 an empty set-up tray 10 that is to be loaded with brackets from carriers 21. Carriers 21 containing brackets 30 are inserted into the holders 44 of the organizer tray 41, with their covers 28 removed, by sliding the flanges 27 onto grooves 45 in the sides of the holders 44, with the handles or tabs 26 of the carriers 21 at the open ends of the holders 44. Each holder 44 receives a carrier 21 containing brackets for a different one of the teeth. The carriers 21 containing the different brackets 30 of a set are loaded into the holders 44 of the organizer tray 41 in the same relative order as the staging areas 15 and 16 are arranged on the set-up card, with the upper bracket carriers 21, carriers 21a, along the side 46 that is adjacent the upper bracket mounting area 13 of the set-up tray 10, while the carriers 21 and with the lower bracket carriers 21, carriers 21b, along the side 47 that is adjacent the lower bracket mounting area 14 of the set-up tray 10. That is, the fourteen holders 44 along the side 46 of the organizer tray 41 contain brackets 30 for the upper teeth, arranged, left to right with brackets for the upper right second molar to the upper left second molar, and the fourteen holders 44 along the side 47 of the organizer tray 41 contain brackets 30 for the lower teeth, arranged, left to right with brackets for the lower right second molar to the lower left second molar.

Figure 3B:
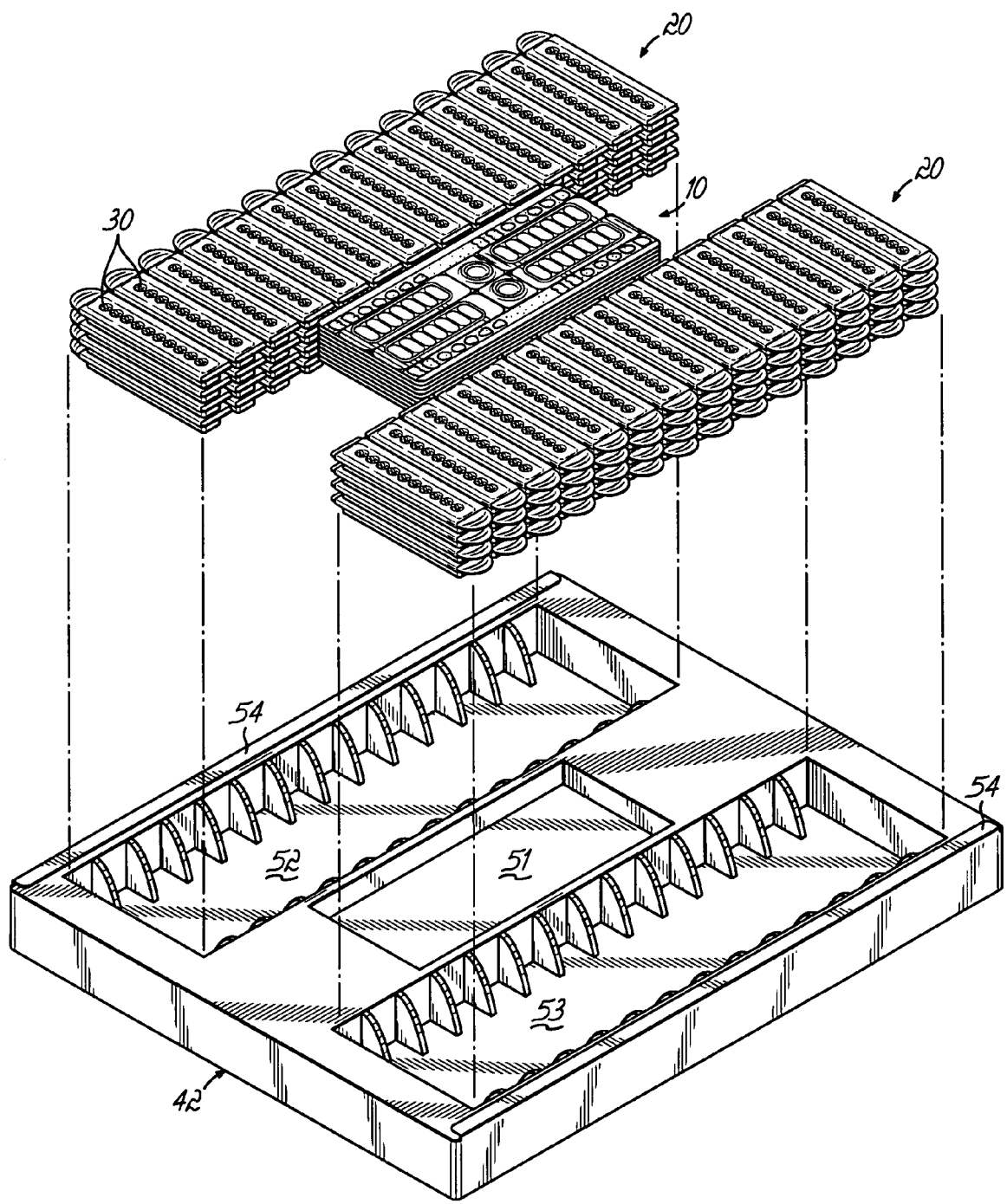
FIG. 3B is a disassembled perspective view of the lower base portion of the organizer of FIG. 3.
Figure 4:
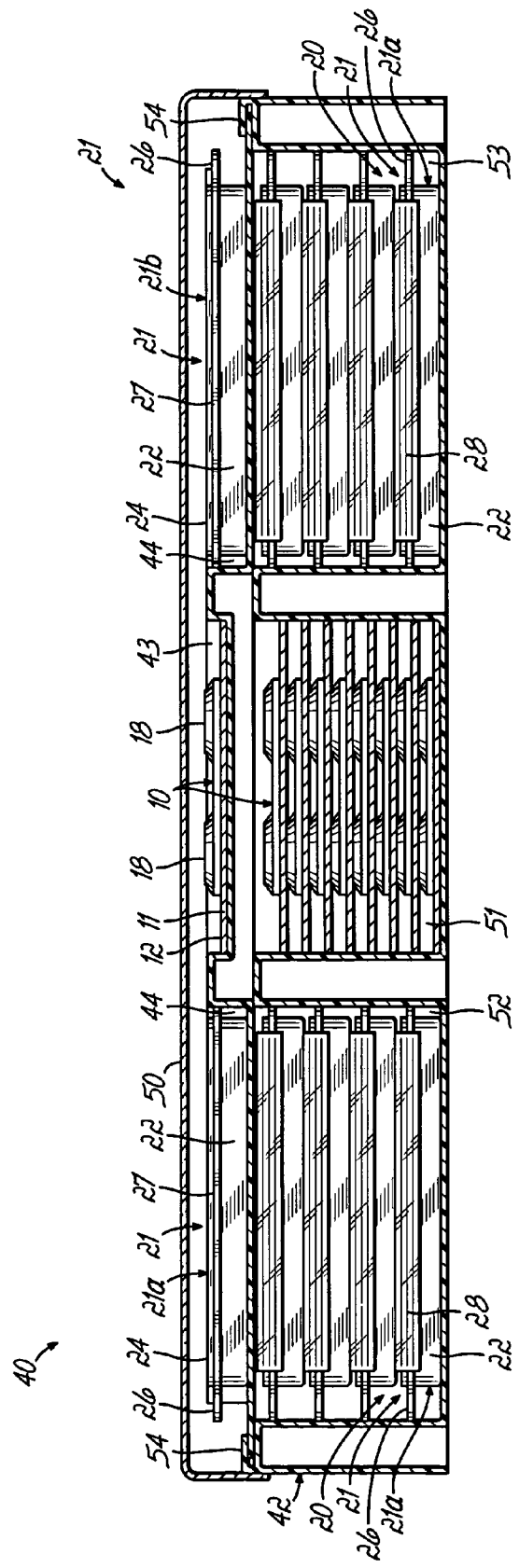
FIG. 4 is a cross-sectional elevational view of the organizer tray of FIG. 3 taken along line 4-4 of FIG. 3.

The base 42 contains hollow storage compartment 51-53, as illustrated in FIGS. 3B and 4. The compartment 51 is directly beneath the recess 43 in the organizer tray 41 when the tray 41 is in a closed position over the base 42 (FIG. 3). The compartment 51 contains a supply of empty set-up trays 10. Similarly, the compartment 52 is directly beneath the holders 44 on side 46 of the organizer tray 41 when the tray 41 is in this closed position and holds a supply of carriers 21a that contain upper brackets 30; and the compartment 53 is directly beneath the holders 44 on side 47 of the organizer tray 41 when in the closed position and holds a supply of carriers 21b that contain lower brackets 30.

Figure 5:
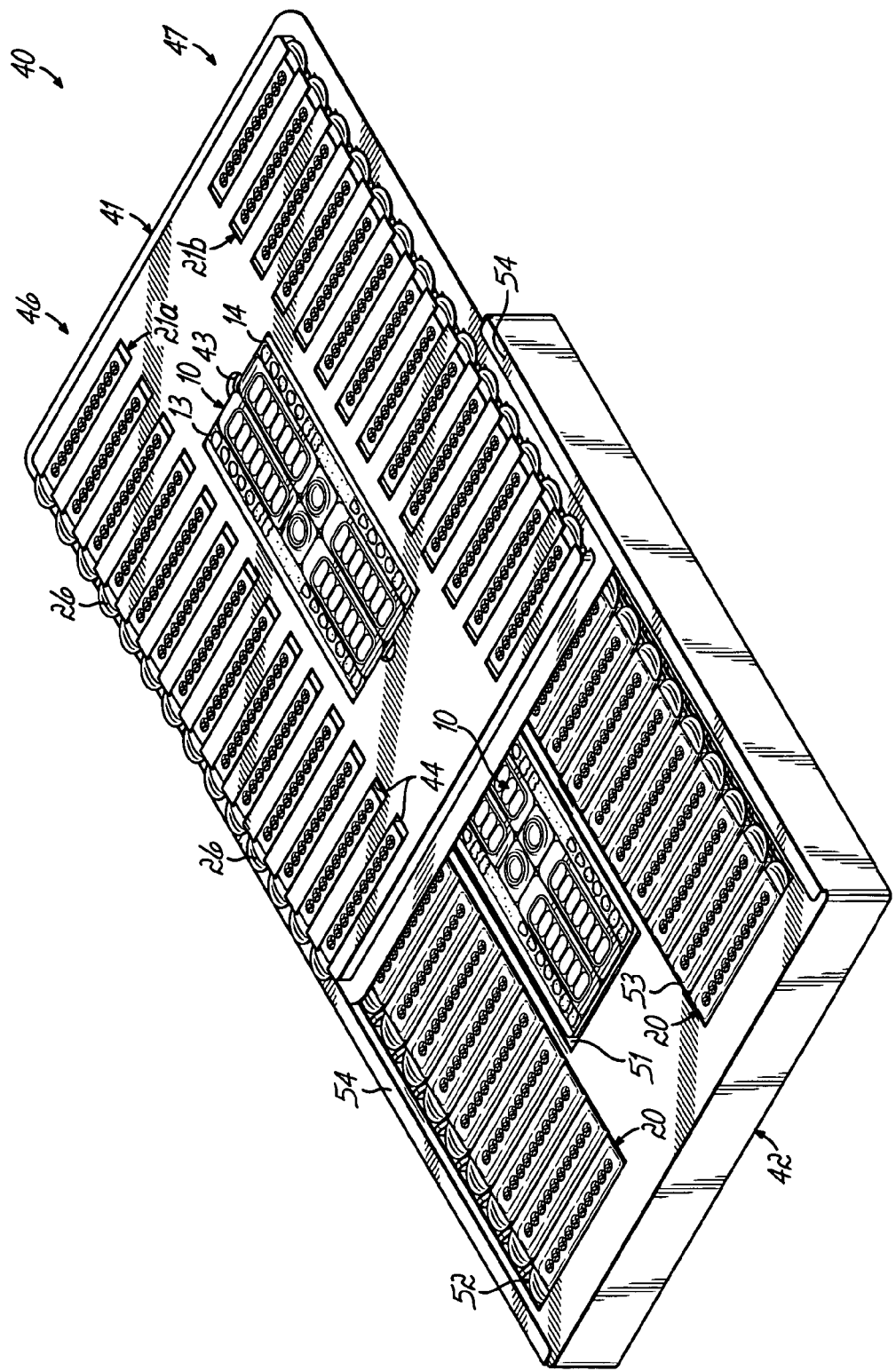
FIG. 5 is a perspective view, similar to FIG. 3, of an organizer in an open condition.

The organizer tray 41 forms a cover to the compartments 51-53 in the base 42, and slides over the base 42 with its outer edges along sides 46 and 47 fitting into grooves 54 along the sides of the base 42 adjacent compartments 52 and 53, respectively. The organizer tray 41 is shown in its closed position over the base 42 in FIG. 3 and in a partially open position in FIG. 5.

Further, a lid 50 may be provided to cover the organizer tray 41 so that the entire organizer 40 can be stored when partially empty carriers 21 are present in the holders 44 of the organizer tray 41. This allows the organizer 40 to be stored in any condition at the office of the orthodontic practitioner. Typically, a slotted cabinet or rack (not shown) is provided at the practitioner's office for storage of organizer trays 40 containing different bracket prescriptions or types.

Figure 6:
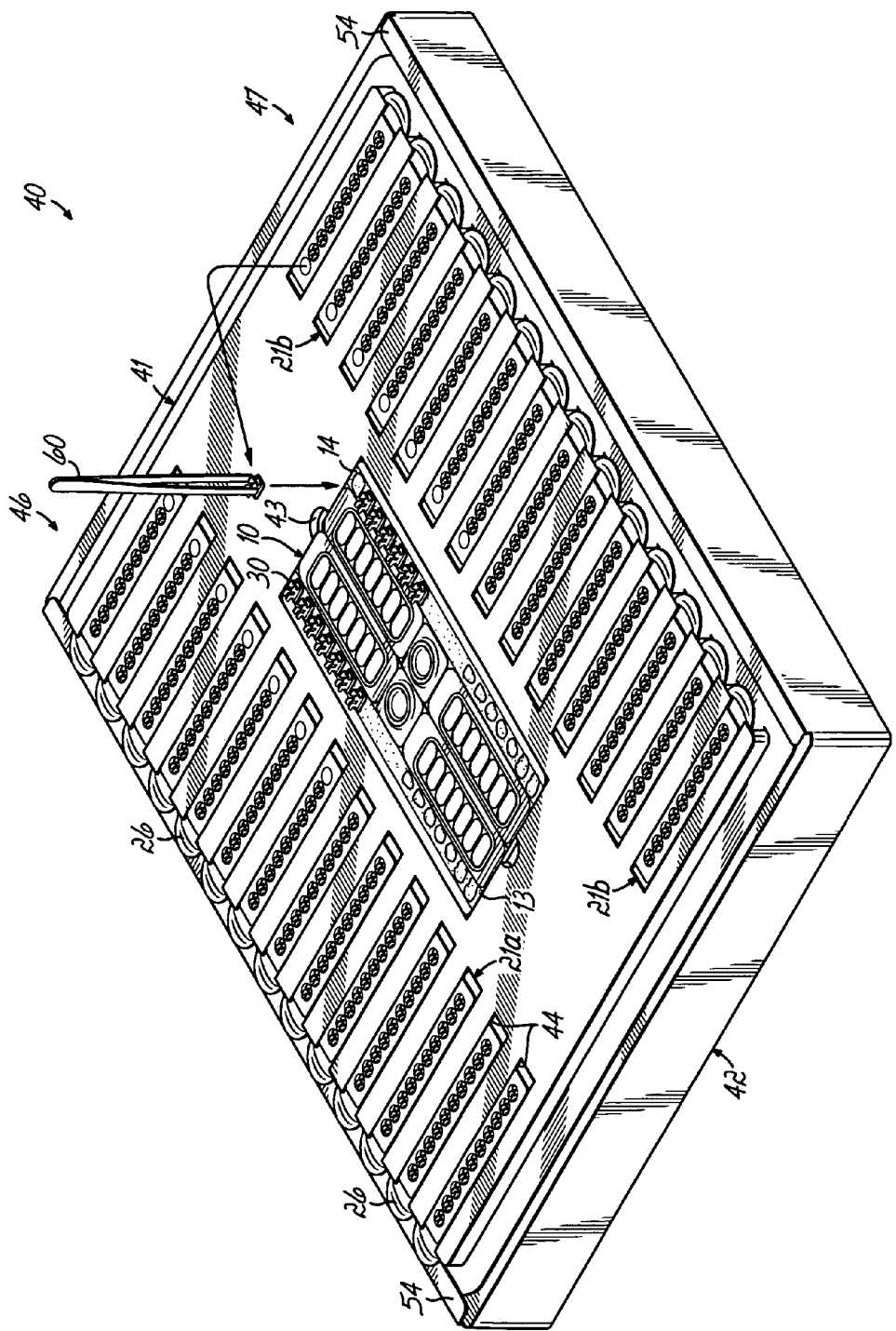
FIG. 6 is a perspective view of the organizer of FIG. 3, showing the organizer in use.
Figure 6A:
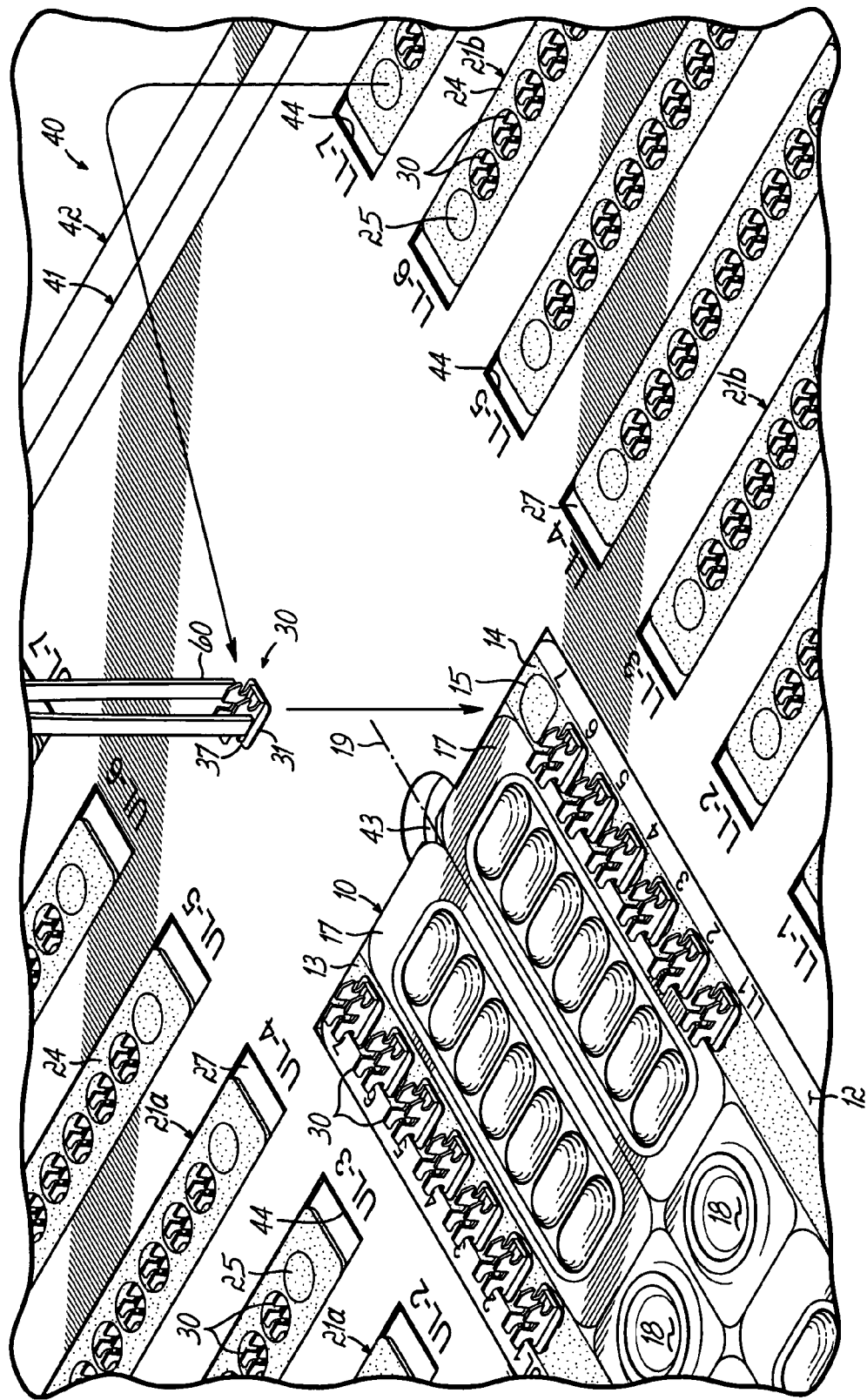
FIG. 6A is an enlarged perspective view of a portion of FIG. 5.

The use of the organizer 40 is illustrated in FIGS. 6 and 6A. The contemplated typical use of the organizer 40 involves the use of the organizer tray 41 by an orthodontic assistant to load a set-up tray 10 with one set of orthodontic brackets 30 to provide to the treating practitioner in installing the brackets 30 on the teeth of a patient. The assistant may use the organizer tray 41 separate from the base 42, or with the base 42 still attached. In loading a set-up tray 10, supported in the recess 43 at the center of the organizer tray 41, the assistant may use an instrument such as a pair of tweezers 60 to transfer each bracket 30 of a set from a hole 25 in a carrier 21 onto a staging area 15 for the particular bracket 30 on the set-up tray 10. The brackets 30 are placed on the staging areas 15 of the set-up tray 10 with their occlusal sides 37 facing the centerline 19 of the set-up tray 10. Because the brackets 30 are provided in the carriers 21 with their gingival edges facing the handles 26 of the carriers 21, and the carriers 21 are loaded into the holders 44 on the organizer tray 41, the brackets 30 are oriented on the organizer tray 41 so their occlusal edges face the centerline 19 of the set-up tray 10 that is supported in the recess 43. Accordingly, a mere translation, with no rotation, is all that is required to load a bracket 30 from a carrier 21 to the set-up card 19.

The organizer tray 41 is, in the prefeffed embodiment, loaded with supplies of brackets 30 from the compartments 52 and 53 beneath the corresponding holders 44 of the tray 41. This loading is carried out by removing one of the packages or carriers 21 from the compartment 52 or 53 and sliding the flanges 27 of the carriers 21 into the slots 45 of the tray 41, with the handles 26 of the carriers 21 facing away from the recess 43 that holds the set-up tray 10. In an alternative embodiment, the carriers 21 and the holders 44 may be configured so that the brackets 30 or other appliances can be transferred from the alternatively configured versions of the packages 21 to alternatively configured versions of the holders 44, with their orientations preferably preserved in the transfer.

When a set-up 10 tray is loaded as described above, an orthodontist may hold the set-up tray 10 with the centerline horizontal and the side holding the bracket mounting areas 13 facing the patient, and then similarly transfer the brackets 30 with tweezers onto the teeth of the patient. Such transfer requires only rotating the pad 31 of the bracket 30 from a horizontal to a vertical plane. Further reorientation of a bracket 30 is not necessary to place the bracket 30 in its correct orientation for mounting on the patients tooth.

The invention has been described in the context of exemplary embodiments. Those skilled in the art will appreciate that additions, deletions and modifications to the features described herein may be made without departing from the principles of the present invention. Accordingly, the following is claimed:

The invention claimed is:

1. A system for organizing orthodontic appliances comprising:
    an orthodontic organizer comprising an orthodontic appliance organizer tray and an orthodontic appliance set up tray;
    the orthodontic appliance organizer tray comprising:
        a generally horizontal upwardly facing surface;
        an orthodontic set-up tray support in a fixed orientation on the upwardly facing surface;
        a plurality of holders on the upwardly facing surface each in a fixed predetermined geometric relationship to the fixed orientation of the set-up tray support;
        each of the holders being configured to rigidly and removably support a plurality of tooth-positioning orthodontic appliances or one or more packages thereof;
        the set-up tray support having a rectangular recess in the upwardly facing surface bounded by four edges each positioned to restrain a set-up tray supported thereon in the fixed orientation on the organizer tray;
    the orthodontic set-up tray being supported in the fixed orientation on the set-up tray support of the orthodontic appliance organizer tray and having thereon a plurality of orthodontic appliance staging areas each configured to support one tooth-positioning orthodontic appliance for transfer to a patient, the plurality of staging areas including one area for each of the teeth of a patient to which a tooth-positioning orthodontic appliance is to be attached in the orthodontic treatment of a patient arranged relative to each other on the set-up tray in a geometric relationship that corresponds to the order of teeth in the mouth of a patient to which the respective appliances are to be attached;
    a plurality of substantially identical, tooth-specific, tooth-positioning orthodontic appliances held in each of the holders in the same predetermined orientation within the respective holder, one appliance of each plurality in the same holder being orthodontically configured for attachment to the same tooth of a patient when used in orthodontic treatment of the patient, with the tooth-specific, tooth-positioning orthodontic appliances held in different holders being orthodontically configured for attachment to different teeth of the patient such that one appliance from each holder forms a single-patient orthodontic appliance set for the orthodontic treatment of a patient;
    the substantially identical, tooth-specific, tooth-positioning orthodontic appliances of each plurality being orthodontic brackets that each have 1) a bonding side for bonding to a tooth and an archwire support side opposite the bonding side on a labial-facial axis, 2) a gingival side and an occlusal side opposite the gingival side on a gingival-occlusal axis perpendicular to the labial-facial axis, and 3) a mesial side and a distal side opposite the mesial side on a mesial-distal axis perpendicular to the gingival-occlusal axis and the labial-facial axis;
    the plurality of holders each holding the respective pluralities of the orthodontic brackets in a predetermined orientation on the organizer tray, with each of the brackets in each respective plurality being held with their respective gingival-occlusal, labial-facial and mesial-distal axes parallel, and with their respective bonding, archwire-supporting, gingival, occlusal, mesial and distal sides facing in the same directions;
    the plurality of holders including a first set of holders for each of a patient's upper teeth arranged in a first predetermined orientation relative to the set-up tray support, and a second set of holders for each of the patient's lower teeth arranged in a second predetermined orientation relative to the set-up tray support that is opposite the first predetermined orientation.

2. A system for organizing orthodontic appliances comprising:
    an orthodontic organizer comprising an orthodontic appliance organizer tray and an orthodontic appliance set up tray;
    the orthodontic appliance organizer tray comprising:
        a generally horizontal upwardly facing surface;
        an orthodontic set-up tray support in a fixed orientation on the upwardly facing surface;
        a plurality of holders on the upwardly facing surface each in a fixed predetermined geometric relationship to the fixed orientation of the set-up tray support;
        each of the holders being configured to rigidly and removably support a plurality of tooth-positioning orthodontic appliances or one or more packages thereof;
        the set-up tray support having a rectangular recess in the upwardly facing surface bounded by four edges each positioned to restrain a set-up tray supported thereon in the fixed orientation on the organizer tray;
    the orthodontic set-up tray being supported in the fixed orientation on the set-up tray support of the orthodontic appliance organizer tray and having thereon a plurality of orthodontic appliance staging areas each configured to support one tooth-positioning orthodontic appliance for transfer to a patient, the plurality of staging areas including one area for each of the teeth of a patient to which a tooth- positioning orthodontic appliance is to be attached in the orthodontic treatment of a patient arranged relative to each other on the set-up tray in a geometric relationship that corresponds to the order of teeth in the mouth of a patient to which the respective appliances are to be attached;
    a plurality of substantially identical, tooth-specific, tooth-positioning orthodontic appliances held in each of the holders in the same predetermined orientation within the respective holder, one appliance of each plurality in the same holder being orthodontically configured for attachment to the same tooth of a patient when used in orthodontic treatment of the patient, with the tooth-specific, tooth-positioning orthodontic appliances held in different holders being orthodontically configured for attachment to different teeth of the patient such that one appliance from each holder forms a single-patient orthodontic appliance set for the orthodontic treatment of a patient;
    the substantially identical, tooth-specific, tooth-positioning orthodontic appliances of each plurality being orthodontic brackets, and the plurality of holders including a first set of holders for each of a patient's upper teeth arranged in a first predetermined orientation relative to the set-up tray support and each holding a package of substantially identical tooth-specific orthodontic brackets for each of the upper teeth of a patient, and a second set of holders for each of the patient's lower teeth arranged in a second predetermined orientation relative to the set-up tray support that is opposite the first predetermined orientation and each holding a package of substantially identical tooth-specific orthodontic brackets for each of the lower teeth of a patient.

3. A system for organizing orthodontic appliances comprising:
an orthodontic organizer comprising an orthodontic organizer tray and an orthodontic set-up tray;
the orthodontic organizer tray comprising:
means for restraining an orthodontic set-up tray in a given orientation on the organizer tray, and
means for holding a plurality of tooth-specific, tooth-positioning orthodontic appliances in a predetermined orientation on the organizer tray in a fixed geometric relationship to the given orientation so that tooth-positioning orthodontic appliances held in the means for holding on the organizer tray can be transferred by translation and without rotation from the means for holding to a set-up tray, restrained by the means for restraining, in the same predetermined orientation with respect to the set-up tray that they had on the organizer tray;
the orthodontic set-up tray being restrained on the orthodontic appliance organizer tray and having thereon a plurality of bracket staging areas thereon, each configured to support an orthodontic bracket for transfer to a patient, the areas each corresponding to one of the teeth of a patient;
a plurality of packages, one held by each of the means for holding, and each including a carrier having a plurality of bracket constraining elements therein;
a plurality of substantially identical, tooth-specific, orthodontic brackets supported in each of the respective carriers, each bracket within each carrier being substantially identical and configured for placement on the same one of a patient's teeth;
the brackets within each package being different from each other and respectively configured for placement on a different one of the patient's teeth;
each package having a cover attached to the carrier to cover the plurality of brackets in each of the appliance constraining elements and removable from the carrier to simultaneously expose each of the plurality of brackets for removal from the bracket constraining elements;
each bracket constraining element of each carrier having one of the plurality of orthodontic brackets therein, each constrained in the same orientation relative to the carrier, the bracket constraining elements snugly holding the respective brackets to the carrier when the cover is removed; and
each carrier having guide structure thereon configured to fix the orientation of the package relative to an organizer tray when the package is loaded onto cooperating structure on the organizer tray and to thereby present the brackets supported on the carrier in the same orientation that is predetermined in relation to the organizer tray.

4. The system of claim 3 wherein:
each of the means for holding includes a pair of parallel, opposed slots in the organizer tray;
each carrier has an elongated recess therein containing the plurality of bracket constraining elements therein;
each bracket constraining element includes a cavity having surfaces shaped to hold one of the orthodontic brackets therein in a fixed orientation relative to the carrier; and
the guide structure includes a flange on the carrier configured to fit into a pair of the slots in an organizer tray to attach the package to the organizer tray in an orientation that is fixed relative to an organizer tray.

5. The system of claim 4 wherein:
each of the bracket constraining elements has a shape configured to hold one of the orthodontic brackets in the cavity when the cavities are uncovered;
the carrier has the flange on opposite sides thereof and has a handle at one end thereof;
each bracket has a bonding base having a gingival edge on one side of the base;
the brackets are each being confined, base down, in each of the cavities with the gingival edge thereof facing the handle of the carrier;
the cover is slidably mounted on the flange so as to be slidably removable from the carrier to simultaneously expose the plurality of brackets and render the brackets accessible for removal from the bracket constraining elements; and
each of the bracket constraining elements includes a cavity having a resilient insert therein having surfaces shaped to snugly hold one of the orthodontic brackets in the cavity when the cover is removed.

6. An orthodontic appliance package comprising:
an elongated carrier having a base with a planar upwardly facing surface having an elongated downwardly extending recess formed therein;
the recess having a plurality of cavities therein arranged on a longitudinal centerline of the elongated recess, the recess having a flexible foam insert therein having the cavities formed therein each dimensioned to receive and to snugly but releasably hold an orthodontic bracket;
the base having a flat flange that extends outwardly in a plane along sides of the recess with a tab handle formed at one end thereof and a pair of straight parallel edges extending along opposite transverse sides thereof for guiding and supporting the package in an organizer tray;
a plurality of tooth-specific orthodontic brackets having substantially identical configurations that adapt the brackets for bonding to the same specific one of a patient's teeth, each bracket having a bonding base with opposite occlusal and gingival edges and opposite mesial and distal edges, each bracket being packaged in the one of the cavities of the carrier with base facing down and oriented with the occlusal edges of their bases facing in the same direction along the longitudinal centerline of the recess; and
an elongated cover having parallel internal channels formed along opposite transverse edges thereof which fit over the flange enclosing the brackets in the cavities and slidably removable from the carrier to expose the brackets for removal from the cavities.

7. An orthodontic appliance package comprising:
an elongated base having an outwardly extending flange defining a pair of straight parallel edges lying in a plane and extending along opposite transverse sides thereof for guiding and supporting the package in an organizer tray, the base having an upper surface with one or more recesses extending downwardly therefrom and having an upwardly facing opening therein, the one or more recesses defining a plurality of cavities arranged longitudinally in a single row along the elongated base;
each of the cavities being accessible through an upwardly facing opening and dimensioned to receive and to snugly but releasably hold an orthodontic bracket;
a plurality of substantially identical tooth-specific orthodontic brackets orthodontically designed for the same specific one of a patient's teeth, each bracket having a bonding base with opposite occlusal and gingival edges and opposite mesial and distal edges, the brackets each being snugly but releasably held in one of the cavities and accessible through the upwardly facing opening, the bonding bases of each bracket facing downwardly, parallel to the plane and oriented with the occlusal edges of the bases of each bracket facing in the same direction.

8. The package of claim 7 wherein the flange forms a handle at one end of the elongated base and the bonding bases of each bracket are oriented with the occlusal edges of the bases of each bracket facing the handle.

9. The package of claim 7 wherein recess is a single recess containing a resilient insert having the cavities formed therein.

10. A system for organizing orthodontic brackets for transfer to a set-up tray, the system comprising a plurality of the packages of claim 7 and further comprising:
  an organizer tray having a generally horizontal upwardly facing surface, an orthodontic set-up tray support area on the upwardly facing surface, and a plurality of holders;
  each of the holders including a pair of parallel opposed grooves configured to receive the parallel edges of the body of one of the packages and supporting one of the packages on the organizer tray;
  each of the holders supporting therein a package having different tooth-specific orthodontic brackets therein orthodontically designed for different specific ones of a patient'teeth;
  the holders being arranged on the organizer tray in two parallel rows, including a first row supporting therein packages having different tooth-specific orthodontic brackets therein orthodontically designed for different specific ones of a patient's upper teeth, and a second row supporting therein packages having different tooth-specific orthodontic brackets therein orthodontically designed for different specific ones of a patient's lower teeth, with the brackets in the packages supported in the first row having the gingival edges of their bases facing in a direction that is opposite from the direction that are facing the gingival edges of the bases of the brackets in the packages supported in the second row.

11. A system for organizing orthodontic brackets for transfer to a set-up tray, the system comprising:
  an organizer tray having a generally horizontal upwardly facing surface, an orthodontic set-up tray support area on the upwardly facing surface, and a plurality of holders arranged thereon;
  each of the holders supporting a package containing a plurality of substantially identical tooth-specific orthodontic brackets orthodontically designed for the same specific one of a patient's teeth, each bracket having a bonding base with opposite occlusal and gingival edges and opposite mesial and distal edges, the bonding bases of each bracket in the package facing in the same direction and oriented with the occlusal edges of the bases of each bracket facing in the same direction;
  each of the packages having different tooth-specific orthodontic brackets therein orthodontically designed for different specific ones of a patient's teeth; and
  the packages supported by the holders including a first group having tooth-specific orthodontic brackets therein orthodontically designed for different specific ones of a patient's upper teeth, and a second group having tooth-specific orthodontic brackets therein orthodontically designed for different specific ones of a patient's lower teeth, with the brackets in the packages of the first group having the gingival edges of their bases facing in a first direction on the organizer tray and the brackets in the packages of the second group having the gingival edges of their bases facing in a second direction that is opposite the first direction on the organizer tray.

12. The system of claim 11 wherein:
  the organizer tray has the plurality of holders arranged thereon in two parallel rows, including a first row and a second row; and
  the packages that are supported by the holders of the first row have the brackets therein oriented on the organizer tray with the gingival edges of their bases facing in a first direction on the organizer tray and the packages that are supported by the holders of the second row have the brackets therein oriented on the organizer tray with the gingival edges of their bases facing in a second direction that is opposite the first direction on the organizer tray.

13. The system of claim 12 further comprising:
  an orthodontic set-up tray supported on the set-up tray support area of the organizer tray and having two rows of orthodontic bracket adhesive-coated staging areas thereon, each adapted to releasably hold one of the orthodontic brackets transferred thereto from a respective one of the packages.

14. The system of claim 11 further comprising:
  an orthodontic set-up tray supported on the set-up tray support area of the organizer tray and having two rows of orthodontic bracket adhesive-coated staging areas thereon, each adapted to releasably hold one of the orthodontic brackets transferred thereto from a respective one of the packages.

15. An orthodontic organizer tray comprising:
  a generally horizontal upper surface having generally parallel first and second edges;
  an orthodontic set-up tray support area on the upper surface, said area having a long dimension oriented parallel to and lying between the first and second edges of the upper surface;
  a plurality of holders arranged in two rows of 10 to 16 holders each, including a first row of holders between and generally parallel to the first edge and the set-up tray support area, and a second row of holders between and generally parallel to the second edge and the set-up tray support area;
  each holder in each respective row having fixed guide structure that is oriented perpendicular to the first and second edges of the upper surface, the fixed guide structure being configured to engage external surfaces of an orthodontic appliance package and constrain the package so engaged in a fixed orientation on the organizer tray; and
  a plurality of packages that each contain a plurality of substantially identical tooth-specific orthodontic brackets each having a pad with a bonding surface configured to bond against the surface of a tooth, with the bonding surfaces of the brackets in each package being oriented relative to the package in a first direction that is the same for each bracket in the package, and with each pad having an occlusal edge designed to face in an occlusal direction on a tooth, with the pads of the brackets in each package being oriented relative to the package in a second direction normal to the first direction and that is the same for each bracket in the package.

16. An orthodontic organizer tray comprising:
  a generally horizontal upper surface having generally parallel first and second edges;

an orthodontic set-up tray support area on the upper surface, said area having a long dimension oriented parallel to and lying between the first and second edges of the upper surface;

a plurality of holders arranged in two rows of 10 to 16 holders each, including a first row of holders between and generally parallel to the first edge and the set-up tray support area, and a second row of holders between and generally parallel to the second edge and the set-up tray support area;

each holder in each respective row having fixed guide structure that is oriented perpendicular to the first and second edges of the upper surface, the fixed guide structure being configured to engage external surfaces of an orthodontic appliance package and constrain the package so engaged in a fixed orientation on the organizer tray; and an orthodontic set-up tray supported on the set-up tray support area of the organizer tray and having two rows of orthodontic bracket adhesive-coated staging areas thereon, each adapted to releasably hold one of the orthodontic brackets transferred thereto from a respective one of the packages.

* * * * *

UNITED STATES PATENT AND TRADEMARK OFFICE
CERTIFICATE OF CORRECTION

| | |
|---|---|
| PATENT NO. | : 7,527,147 B2 |
| APPLICATION NO. | : 10/781138 |
| DATED | : May 5, 2009 |
| INVENTOR(S) | : Kevin Corcoran et al. |

It is certified that error appears in the above-identified patent and that said Letters Patent is hereby corrected as shown below:

In Column 3, line 13, "orthodontist, and, if" should read -- orthodontist and, if --.

In Column 5, line 14, "as carriers and 21a and 21b," should read -- as carriers 21a and 21b, --.

In Column 6, line 42, "in the prefeffed embodiment," should read -- in the preferred embodiment, --.

In claim 10, Column 11, line 38, "in a direction that is opposite from the direction that are" should read -- in a direction that is opposite from the direction in which are --.

Signed and Sealed this

Sixteenth Day of March, 2010

David J. Kappos
*Director of the United States Patent and Trademark Office*